(12) United States Patent
Morita et al.

(10) Patent No.: US 7,331,929 B2
(45) Date of Patent: Feb. 19, 2008

(54) METHOD AND APPARATUS FOR SURGICAL OPERATING ROOM INFORMATION DISPLAY GAZE DETECTION AND USER PRIORITIZATION FOR CONTROL

(75) Inventors: Mark M. Morita, Arlington Heights, IL (US); Prakash Mahesh, Schaumburg, IL (US); Thomas A. Gentles, Algonquin, IL (US)

(73) Assignee: General Electric Company, Schenectady, NY (US)

( * ) Notice: Subject to any disclaimer, the term of this patent is extended or adjusted under 35 U.S.C. 154(b) by 245 days.

(21) Appl. No.: 10/956,435

(22) Filed: Oct. 1, 2004

(65) Prior Publication Data

US 2006/0082542 A1    Apr. 20, 2006

(51) Int. Cl.
| | |
|---|---|
| *A61B 13/00* | (2006.01) |
| *A61B 5/103* | (2006.01) |
| *A61B 5/117* | (2006.01) |
| *A61B 5/04* | (2006.01) |
| *A61B 3/14* | (2006.01) |
| *A61B 3/10* | (2006.01) |
| *G03B 17/00* | (2006.01) |
| *H04N 5/222* | (2006.01) |
| *G06K 9/00* | (2006.01) |
| *A63F 9/24* | (2006.01) |
| *A63F 13/00* | (2006.01) |
| *G06F 17/00* | (2006.01) |
| *G06F 19/00* | (2006.01) |

(52) U.S. Cl. ............... 600/558; 600/383; 600/587; 600/595; 351/208; 351/209; 351/211; 396/51; 348/333.03; 382/115; 382/117; 463/7

(58) Field of Classification Search ......... 600/558, 600/383, 587, 595; 351/209, 208, 211; 396/51; 348/333.03; 382/115, 117; 463/7
See application file for complete search history.

(56) References Cited

U.S. PATENT DOCUMENTS

| | | | | |
|---|---|---|---|---|
| 4,931,865 A | * | 6/1990 | Scarampi | 725/12 |
| 6,106,119 A | * | 8/2000 | Edwards | 351/209 |
| 6,152,563 A | | 11/2000 | Hutchinson et al. | |

(Continued)

FOREIGN PATENT DOCUMENTS

| | | | |
|---|---|---|---|
| WO | WO 03/023756 | | 3/2003 |
| WO | WO 03/050658 A2 | * | 6/2003 |

OTHER PUBLICATIONS

"Cardio-Thoracic Surgeons First to Evaluate Md-6 Critical Data Viewer for Viewing Patient Monitoring Data," Microoptical to Introduce MD-6 Critical Data Viewer at the 40th Annual Meeting and Exhibition for the Society of Thoracic Surgeons, pp. 1-2, (Jan. 19, 2004).XP002357646.

(Continued)

*Primary Examiner*—Max Hindenburg
*Assistant Examiner*—Jeffrey G Hoekstra
(74) *Attorney, Agent, or Firm*—McAndrews, Held & Malloy, Ltd.; Peter J. Vogel; Michael A. Dellapenna (57) ABSTRACT

Certain embodiments of the present invention provide a method and system for using gaze detection to improve information display in a healthcare environment. Certain embodiments of a system include an eyewear headset for detecting a location of a user's gaze and a display for displaying information. Information on the display, such as images and/or data, is customized for the user based on the user's gaze. In an embodiment, the eyewear headset viewer projects information into the user's oculars for an individual information display. The system may also include a conflict resolution module for determining priority and control of the display among a plurality of users. In an embodiment, a function at the display may be triggered using a voice command, a gesture, and/or a gaze, for example.

11 Claims, 4 Drawing Sheets

U.S. PATENT DOCUMENTS

| | | |
|---|---|---|
| 6,349,001 B1 | 2/2002 | Spitzer |
| 6,384,982 B1 | 5/2002 | Spitzer |
| 6,539,100 B1 * | 3/2003 | Amir et al. .................. 382/117 |
| 6,712,468 B1 * | 3/2004 | Edwards ..................... 351/209 |
| 7,113,170 B2 * | 9/2006 | Lauper et al. .............. 345/158 |
| 2004/0061831 A1 | 4/2004 | Aughey et al. |
| 2005/0004496 A1 * | 1/2005 | Pilu et al. ................... 600/595 |

OTHER PUBLICATIONS

"MD-6 Critical Data Viewer Enables Anesthesiologists to Monitor Critical Data While Maintaining their Focus on the Patient," Anesthesiologist Present Test Results on Microoptical's Critical Data Viewer at Medicine Meets Virtual Reality conference, pp. 1-2 (Jan. 20, 2004). XP002357647.

MD-6 Critical Data Viewer for Surgeons, pp. 1-4 (2004). XP002357648.

"Anesthesiology Pioneers New Direction in Telemedicine," The Reporter, pp. 1-4 (Apr. 2, 2004).XP002357649.

International Search Report for EP 05 25 6084 (Dec. 27, 2005).

Web page for SensoMotoric Instruments, http://www.smi.de/iv/index.html, Oct. 1, 2004.

Web page for MicroOptical, http://www.microoptical.net/Products/HomePage.html, Oct. 1, 2004.

* cited by examiner

METHOD AND APPARATUS FOR SURGICAL OPERATING ROOM INFORMATION DISPLAY GAZE DETECTION AND USER PRIORITIZATION FOR CONTROL

BACKGROUND OF THE INVENTION

The present invention generally relates to display of information in a healthcare environment. In particular, the present invention relates to use of gaze detection technology to improve display of relevant information in a healthcare environment.

A clinical or healthcare environment is a crowded, demanding environment that would benefit from organization and improved ease of use of imaging systems, data storage systems, and other equipment used in the healthcare environment. A healthcare environment, such as a hospital or clinic, encompasses a large array of professionals, patients, and equipment. Personnel in a healthcare facility must manage a plurality of patients, systems, and tasks to provide quality service to patients. Healthcare personnel may encounter many difficulties or obstacles in their workflow.

A variety of distractions in a clinical environment may frequently interrupt medical personnel or interfere with their job performance. Furthermore, workspaces, such as a radiology workspace, may become cluttered with a variety of monitors, data input devices, data storage devices, and communication device, for example. Cluttered workspaces may result in efficient workflow and service to clients, which may impact a patient's health and safety or result in liability for a healthcare facility. Data entry and access is also complicated in a typical healthcare facility.

Thus, management of multiple and disparate devices, positioned within an already crowded environment, that are used to perform daily tasks is difficult for medical or healthcare personnel. Additionally, a lack of interoperability between the devices increases delay and inconvenience associated with the use of multiple devices in a healthcare workflow. The use of multiple devices may also involve managing multiple logons within the same environment. A system and method for improving ease of use and interoperability between multiple devices in a healthcare environment would be highly desirable.

In a healthcare environment involving extensive interaction with a plurality of devices, such as keyboards, computer mousing devices, imaging probes, and surgical equipment, repetitive motion disorders often occur. A system and method that eliminate some of the repetitive motion in order to minimize repetitive motion injuries would be highly desirable.

Healthcare environments, such as hospitals or clinics, include clinical information systems, such as hospital information systems (HIS) and radiology information systems (RIS), and storage systems, such as picture archiving and communication systems (PACS). Information stored may include patient medical histories, imaging data, test results, diagnosis information, management information, and/or scheduling information, for example. The information may be centrally stored or divided at a plurality of locations. Healthcare practitioners may desire to access patient information or other information at various points in a healthcare workflow. For example, during surgery, medical personnel may access patient information, such as images of a patient's anatomy, that are stored in a medical information system. Alternatively, medical personnel may enter new information, such as history, diagnostic, or treatment information, into a medical information system during an ongoing medical procedure.

In current information systems, such as PACS, information is entered or retrieved using a local computer terminal with a keyboard and/or mouse. During a medical procedure or at other times in a medical workflow, physical use of a keyboard, mouse or similar device may be impractical (e.g., in a different room) and/or unsanitary (i.e., a violation of the integrity of an individual's sterile field). Re-sterilizing after using a local computer terminal is often impractical for medical personnel in an operating room, for example, and may discourage medical personnel from accessing medical information systems. Thus, a system and method providing access to a medical information system without physical contact would be highly desirable to improve workflow and maintain a sterile field.

Imaging systems are complicated to configure and to operate. Often, healthcare personnel may be trying to obtain an image of a patient, reference or update patient records or diagnosis, and ordering additional tests or consultation. Thus, there is a need for a system and method that facilitate operation and interoperability of an imaging system and related devices by an operator.

In many situations, an operator of an imaging system may experience difficulty when scanning a patient or other object using an imaging system console. For example, using an imaging system, such as an ultrasound imaging system, for upper and lower extremity exams, compression exams, carotid exams, neo-natal head exams, and portable exams may be difficult with a typical system control console. An operator may not be able to physically reach both the console and a location to be scanned. Additionally, an operator may not be able to adjust a patient being scanned and operate the system at the console simultaneously. An operator may be unable to reach a telephone or a computer terminal to access information or order tests or consultation. Providing an additional operator or assistant to assist with examination may increase cost of the examination and may produce errors or unusable data due to miscommunication between the operator and the assistant. Thus, a method and system that facilitate operation of an imaging system and related services by an individual operator would be highly desirable.

A reading, such as a radiology or cardiology procedure reading, is a process of a healthcare practitioner, such as a radiologist or a cardiologist, viewing digital images of a patient. The practitioner performs a diagnosis based on a content of the diagnostic images and reports on results electronically (e.g., using dictation or otherwise) or on paper. The practitioner, such as a radiologist or cardiologist, typically uses other tools to perform diagnosis. Some examples of other tools are prior and related prior (historical) exams and their results, laboratory exams (such as blood work), allergies, pathology results, medication, alerts, document images, and other tools. For example, a radiologist or cardiologist typically looks into other systems such as laboratory information, electronic medical records, and healthcare information when reading examination results.

Currently, a practitioner must log on to different systems and search for a patient to retrieve information from the system on that patient. For example, if a patient complains of chest pain, a chest x-ray is taken. Then the radiologist logs on to other systems to search for the patient and look for specific conditions and symptoms for the patient. Thus, the radiologist may be presented with a large amount of information to review.

Depending upon vendors and systems used by a practitioner, practitioners, such as radiologists or cardiologists, have only a few options to reference the tools available. First, a request for information from the available tools may be made in paper form. Second, a practitioner may use different applications, such as a radiologist information system (RIS), picture archiving and communication system (PACS), electronic medical record (EMR), healthcare information system (HIS), and laboratory information system (LIS), to search for patients and examine the information electronically.

In the first case, the practitioner shifts his or her focus away from a reading workstation to search and browse through the paper, which in most cases includes many pieces of paper per patient. This slows down the practitioner and introduces a potential for errors due to the sheer volume of paper. Thus, a system and method that reduce the amount of paper being viewed and arranged by a practitioner would be highly desirable.

In the second case, electronic information systems often do not communicate well across different systems. Therefore, the practitioner must log on to each system separately and search for the patients and exams on each system. Such a tedious task results in significant delays and potential errors. Thus, a system and method that improve communication and interaction between multiple electronic information systems would be highly desirable.

Additionally, even if systems are integrated using mechanisms such as Clinical Context Object Workgroup (CCOW) to provide a practitioner with a uniform patient context in several systems, the practitioner is still provided with too much information to browse through. Too much information from different applications is provided at the same time and slows down the reading and analysis process. There is a need to filter out application components that a user will not need in a routine workflow. Thus, a system and method which manage information provided by multiple systems would be highly desirable.

Currently, a healthcare environment such as an operating room (OR) includes multiple displays (CRT, LCD, etc.) connected to multiple, disparate information and/or imaging systems. The displays may be hanging on boom mounted arms from walls, ceilings, tables, and/or floors, for example. In some healthcare settings, such as an OR, ten or more displays may clutter the room and cause great difficulty for practitioners trying to locate key information without scanning each display.

When practitioners wish to access information from the disparate systems, the practitioners must currently turn their heads to look up at the multiple displays and determine which display holds the desired information. Head movement, particularly during a medical procedure, is neither ergonomically correct nor comfortable for the practitioner. Additionally, such head movement may be very repetitive throughout an examination or procedure. Thus, a system and method which reduce head movement and improves ergonomics in a healthcare environment would be highly desirable.

In addition, multiple displays results in an overabundance of information presented simultaneously to a healthcare practitioner. Thus, too much information on too many displays creates difficulty for a practitioner attempting to locate relevant information. Therefore, there is a need for a system and method to improve identification of key information and reduce display clutter in a healthcare environment.

Further difficulties may arise from having too many displays in a healthcare environment, such as an OR. For example, multiple displays are not cost effective from an information technology perspective. Purchasing multiple displays for one or more rooms represents a significant expense for a healthcare provider. Additionally, for example, multiple displays and/or multiple systems generate additional heat in a healthcare environment. Excess heat contributes to higher electric bills and may pose a health hazard to patients, practitioners, and equipment in a healthcare environment. Therefore, a system that reduces multiple displays in a healthcare environment would be highly desirable.

Thus, there is a need for a system and method to improve display of relevant information in a healthcare environment.

BRIEF SUMMARY OF THE INVENTION

Certain embodiments of the present invention provide a method and system for using gaze detection to improve information display in a healthcare environment. Certain embodiments of a system include an eyewear headset for detecting a location of a user's gaze and a display for displaying information. Information on the display, such as images and/or data, is customized for the user based on the user's gaze. In an embodiment, the eyewear headset viewer projects information into the user's oculars for an individual information display. The system may also include a conflict resolution module for determining priority and control of the display among a plurality of users. In an embodiment, a function at the display may be triggered using a voice command, a gesture, and/or a gaze, for example.

In an embodiment, the system also includes a plurality of perspectives that each save a relation with at least one of a plurality of information sources. The system may also include a medical perspectives manager for associating at least one information source with a perspective. The medical perspectives manager allows a user to access the associated information source(s) using the perspective.

In an embodiment, the system also includes a rules engine that has at least one rule governing availability and/or presentation of information. The system may also include a context manager for obtaining information from the plurality of information sources based on a query and filtering the information based on the rule(s) from the rules engine.

Certain embodiments of a method include determining a direction of a user's gaze in relation to a reference position, identifying a user looking toward a display, and updating information on the display based on the user. In an embodiment, information is updated on the display based on preferences and/or input from the user, for example.

The method may also include arbitrating between a plurality of users to determine who has control of the display. In an embodiment, multiple users may be allowed control of information on all or part of the display. A function may be triggered at the display using a voice command, a gesture, and/or a gaze, for example. Additionally, the method may include projecting an image into a user's oculars. The method may further include defining at least one perspective that personalizes information relevant to the user. In an embodiment, information available on the display is filtered based on one or more rules.

In an embodiment, a computer-readable storage medium includes a set of instructions for a computer directed to displaying information. The set of instructions includes a gaze detection routine for determining when a user is looking at a display, and a display routine for displaying, on the display, information associated with the user when the user is looking at the display. The set of instructions may also include a selection routine for selecting information associated with a user. Additionally, the set of instructions may include an arbitration routine for determining priority of control among a plurality of users looking at the display. The set of instructions may also include a rules-based context manager for filtering the information associated with the user based on at least one rule. In an embodiment, the information includes data and/or image(s), for example.

The foregoing summary, as well as the following detailed description of certain embodiments of the present invention, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

Figure 1:
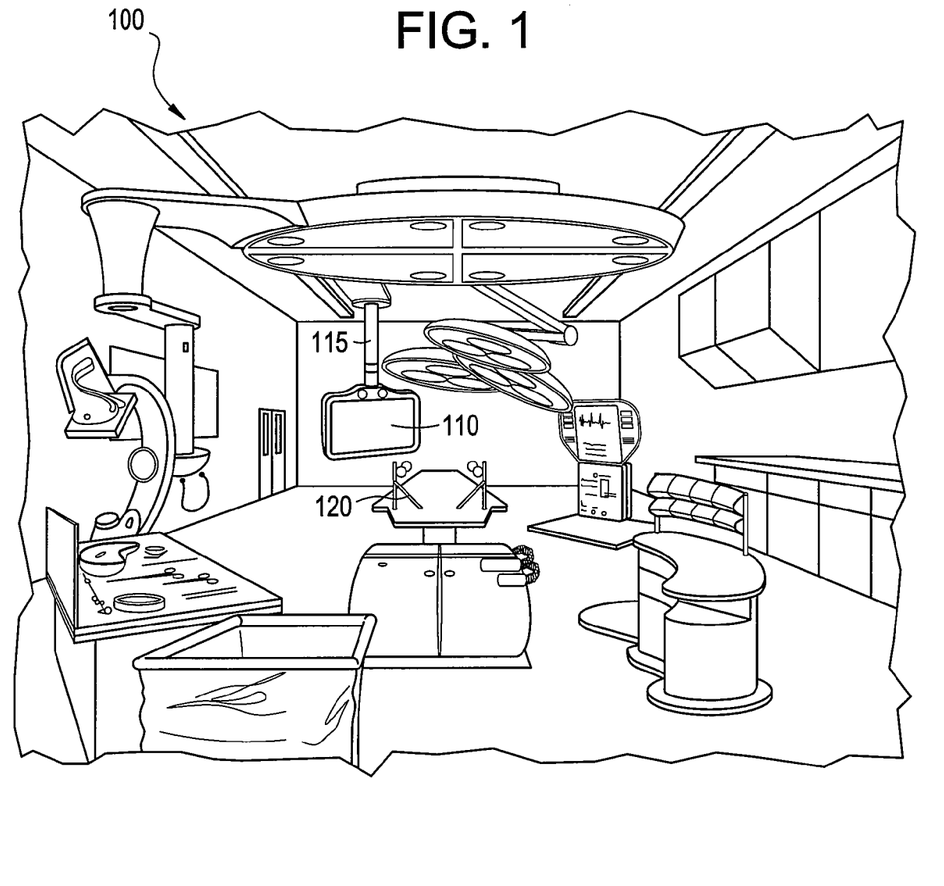
FIG. 1 illustrates an improved operating room used in accordance with an embodiment of the present invention.

FIG. 1 illustrates an improved operating room 100 used in accordance with an embodiment of the present invention. As shown in FIG. 1, numerous disparate displays have been replaced with a single, large format display 110 suspended on a boom 115 near an operating table 120. The display 110 may be used with a portable eyewear and eye tracking system to display information for a plurality of users. Additionally, voice commands and/or gesture control using cameras, such as fire-wire web cams, may allow interaction with imaging and information systems without disrupting a sterile field.

Figure 2:
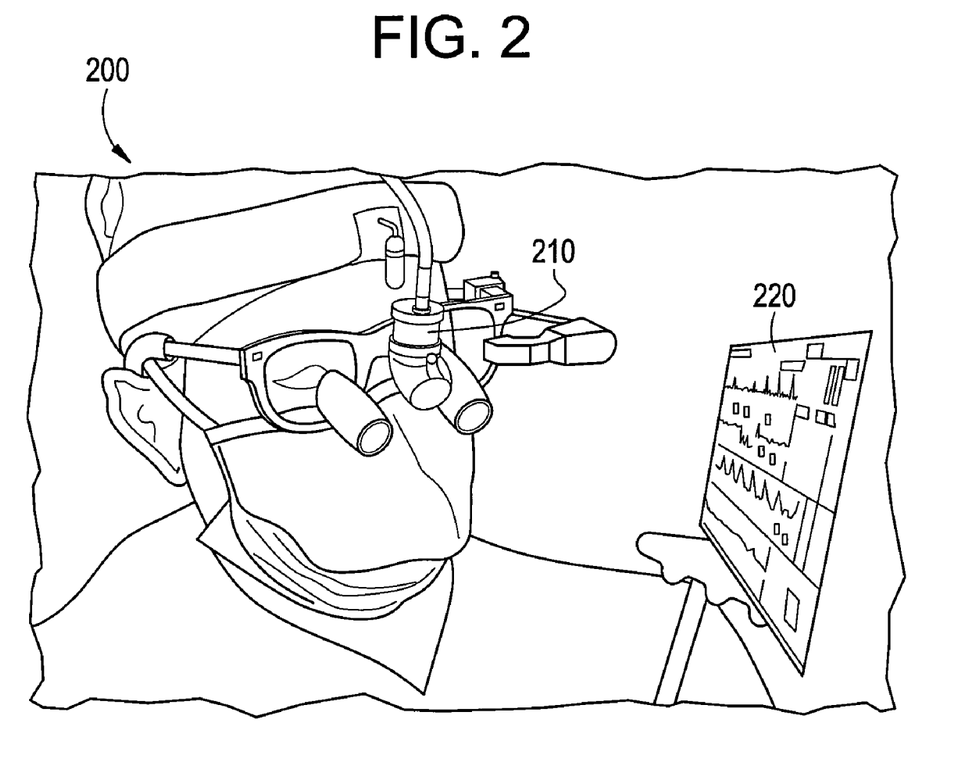
FIG. 2 depicts a portable eyewear viewing system used in accordance with an embodiment of the present invention.

FIG. 2 depicts a portable eyewear viewing system 200 used in accordance with an embodiment of the present invention. The system 200 includes an eyewear headset 210, a personal eyewear display 220, and a gaze tracking processor 230. The processor 230 may be integrated into the eyewear 210 and/or separate from the eyewear 210. The personal eyewear display 220 is projected in a user's field of view by the eyewear 210.

A healthcare practitioner may use eyewear 210, such as goggles, to capture the practitioner's gaze and perform interface navigation. A user's gaze may be tracked via infrared or other light source, for example. Light may be reflected off of the user's pupil(s) and detected. Light may also be reflected off of the front and rear surfaces of the cornea(s) and lenses of the user's eye(s) and detected or recorded. Repeated measurements track a change in the user's gaze. Alternatively or in addition, a user's gaze may be tracked based on movement of the user's head via a camera or position sensor, for example. A position of the user's gaze and/or head in a reference coordinate system and/or with respect to a reference point, such as a location on a display, may be determined. In an embodiment, a plurality of measurements may be obtained to determine a user's line of sight and/or head angle, for example.

Goggles or other eyewear may also project images into a user's oculars or provide a miniature screen attached to the eyewear 210 and positioned in the user's field of vision to form a virtual personal display 220. Thus, eyewear 210 may be used to eliminate some displays in the healthcare environment. Additionally, eyewear 210 may allow specific information to be targeted for display for specific users in the healthcare environment. For example, a nurse, an anesthesiologist, and a surgeon receive different information displayed on their personal eyewear display 220. For example, a surgeon may view image-guided surgery and PACS data while an anesthesiologist views EKG and dosage data. In an embodiment, each user may view customized information without turning to look at a display to select the information.

In an embodiment, the eyewear 210 is a portable eyewear viewer that displays key dynamic patient information such as hemodynamic data, cardiology waveforms, vital signs, etc. Eyewear 210 allows a user to view information without turning his or her head to view an LCD or CRT monitor. Although the eyewear headset 210 allows users to view data while working "heads down" on a patient, resolution may be limited for image review and/or fine text review, for example. When a user wishes to view detailed information or a finer degree of granularity, the user may look at a single large format display in the healthcare environment. In an embodiment, the eyewear headset 210 and/or processor 230 include eye-tracking software so that once the software detects that a user is gazing at the large format display, the user's perspectives and/or rules-based information is displayed on the screen. Eye tracking capability of the headset 210 and/or processor 230 may also use gaze directional input to control the large format display. For example, the processor 230 detects when a user is looking at a certain button, option or feature on a display and selects or activates the button, option or feature for the user. Activation of an option/feature may also be based on an amount of time a user is looking at a certain area. The eyewear system 200 may also be used in conjunction with voice commands and/or gestures to control the display 220 and/or other systems or features, for example.

For example, based on a system of rules, a chief surgeon has prioritized viewing rights to the large format display. Once the chief surgeon returns to "heads down" surgery, the display is available for access by other users. In an embodiment, "hanging" display protocols allow users to share real estate on the large format display.

Figure 3:
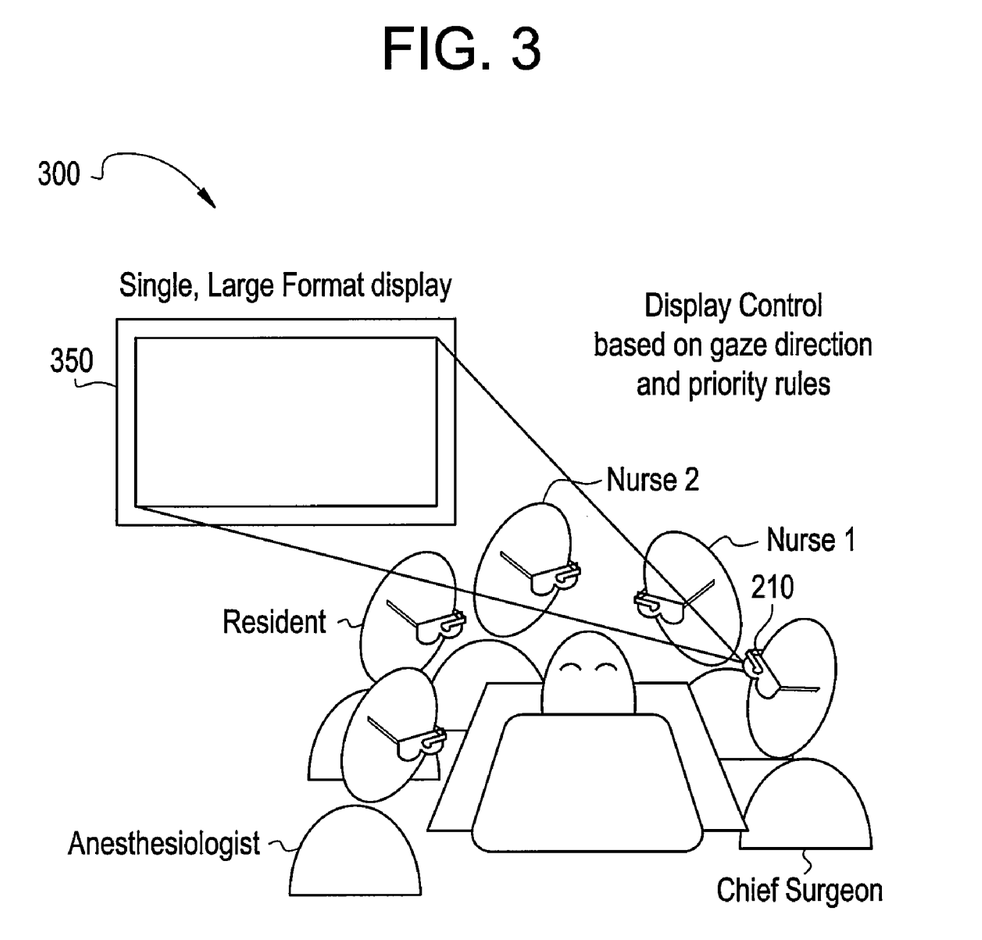
FIG. 3 illustrates a gaze detection and control system used in accordance with an embodiment of the present invention.

FIG. 3 illustrates a gaze detection and control system 300 used in accordance with an embodiment of the present invention. The system 300 includes a single large display 350 and a plurality of eyewear 210. The system 300 may include a gaze tracking and control processor 360 (not shown) which is a separate processor or a coordinated network of gaze tracking processors 230. In an embodiment, the personal eyewear display 220 may have limited resolution, such as 600×800 or 800×600. Thus, certain information, such as patient vital signs and other data, the personal eyewear display 220 offers sufficient resolution. For larger information, a single large display 350 may be referenced by a practitioner to view the larger information, such as image-guided surgery information. The user looks at the display 350. The gaze tracking processor 230 recognizes that the user wants to see certain information and displays context-sensitive information for the patient on the larger display 350 using perspectives, for example. Information on gaze and/or head position may be relayed from the processor 230 to determine information on the display 350. Additionally, user preference information, information from the display 220, and/or other input may be transmitted to configure the contents and/or other parameters of the display 350.

In an embodiment, information displayed on the display 350 may be determined based on rules in place or in addition to perspectives. For example, rules determine that a doctor's gaze takes precedence over a nurse's gaze. Then, when the doctor turns away from the display 350, the nurse gains control of the display 350. Alternatively, control of the display 350 may be shared by multiple users and common information displayed on display 350 so that multiple users may be accommodated at approximately the same time.

Thus, the systems 200 and 300 allow a user to access and display data from a variety of systems, such as PACS, EMR, LIS, HIS, RIS, CVIS, and other applications or systems. The processors 230 and/or 360 organize data into views useful for individual viewers. The processors 230 and/or 360 recognize quickly that a user is gazing at the large display 350 and projects the user's information on the display 350. Additionally, the processors 230 and/or 360 may have an ability to arbitrate conflicts and priority among a plurality of users seeking access determine which user(s) should take control of the display 350. For example, rules-based display control and/or hanging protocols may govern which user has control and priority and/or which users may share control and display area. Rules and other protocols may also govern when control over the display 350 is relinquished and/or pre-empted.

The display 350 replaces multiple displays in an OR. The display system 300 tracks a user's gaze and, based on the user's preferences, presents user-specified "perspectives based" enterprise information when the user wants more detailed information than the portable eyewear viewer 220 resolution allows. For example, clearer text and/or anatomical imagery may be seen by the user on the display 350 when desired. Information displayed on the display 350 may complement and/or replace information displayed in the eyewear headset display 220.

In an embodiment, video switchboxes and/or voice commands may be used with image-guided surgery to switch displays so that only image-guided surgery information is viewed. In an embodiment, voice control and/or gestures may be used in conjunction with eye tracking to control the display 350 and/or a system cursor.

In an embodiment, the manager 120 may work together with a rules-based context manager to filter and display information. One example of a rules-based context manager is described in a U.S. Patent Application filed on Oct. 1, 2004, entitled "System and Method for Rules-Based Context Management in Radiology and Cardiology Diagnostic Reading", with inventor Prakash Mahesh, which is herein incorporated by reference in its entirety.

In an embodiment, the manager 120 may work together with a perspectives management system for handling multiple applications and workflow. The perspectives management system allows various perspectives to be defined which save workflow steps and other information for a particular user. Perspectives allow a personalized information display to present relevant information germane to a patient's current condition, for example. One example of a perspectives management system is described in a U.S. Patent Application filed on Oct. 1, 2004, entitled "System and Method for Handling Multiple Radiology Applications and Workflows", with inventors Prakash Mahesh and Mark Ricard, which is herein incorporated by reference in its entirety. For example, in a surgical OR there may be numerous healthcare practitioners at an OR table who use specific perspectives or views of relevant patient information. With a single, large format display (e.g., an LCD, plasma display, 46"+display, etc.), each user has the ability to view their personal perspectives on the display in large and/or small format. The display may be shared among the users.

Figure 4:
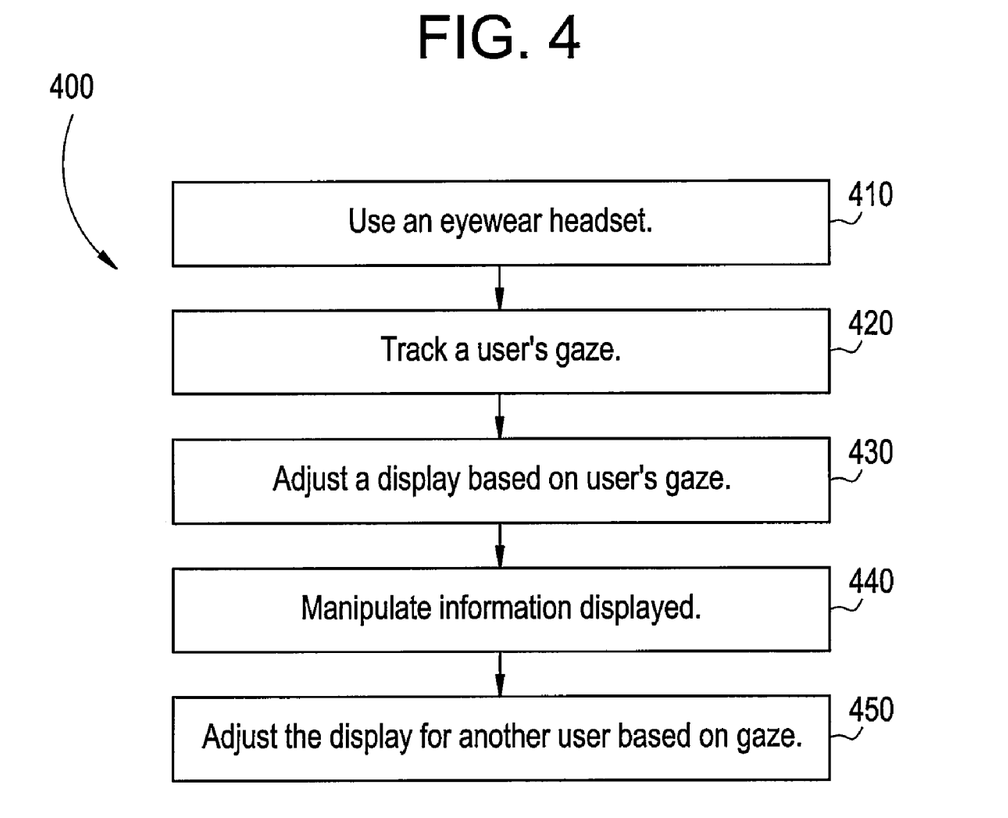
FIG. 4 shows a flow diagram for a method for gaze detection and control in a healthcare environment used in accordance with an embodiment of the present invention.

FIG. 4 shows a flow diagram for a method 400 for gaze detection and control in a healthcare environment used in accordance with an embodiment of the present invention. First, at step 410, a user wears an eyewear headset, such as the portable eyewear 210. Then, at step 420, a user's gaze is tracked via the eyewear. For example, the user's gaze may be tracked on the eyewear display 220 to select certain information and/or features on the display 220. Additionally, for example, the user's gaze may be tracked on the display 350.

At step 430, when the user's gaze is detected toward the display 350, content on the display 350 is adjusted to accommodate the user. That is, context-sensitive perspectives and/or rules may be used to display relevant information for the particular user on the display 350. Space on the display 350 may devoted entirely to a single user who is looking at the display 350 or may be divided to display data for multiple users. Alternatively, the display 350 may include an area displaying general data and one or more areas displaying data specific to a certain user. In an embodiment, if multiple users are looking toward the display 350, user priority may be compared to determine which user(s) are allowed to take control of the display 350.

Then, at step 440, the user controlling the display 350 may manipulate the display 350. For example, the user may adjust information shown on the display 350 based on gaze, voice command, gesture, button, switch, and/or mousing device. The user may similarly adjust information displayed on the display 220. Information shown on the display 220 may or may not mimic information shown on the display 220.

Next, at step 450, when the user redirects his or her gaze away from the display 350, the display 350 adjusts itself for another user. For example, when a surgeon looks from the display 350 back down to a patient undergoing a surgical procedure, the display 350 becomes available for a nurse to display information. In an embodiment, information such as vital signs may be continuously displayed via personal eyewear worn by the users in the environment. Information displayed on the display 350 supplements and/or enhances the information displayed on the eyewear displays 220.

Thus, certain embodiments unify a variety of information systems and other applications in a single display viewable by a plurality of users. Certain embodiments filter information available to a user based on rules and/or perspectives. Certain embodiments address information overload, ergonomic issues, and effects from multiple displays such as clutter, heat, expense, and luminosity from displays, for example. Multiple displays may be eliminated from a healthcare environment, such as an OR, and information on the single large display may be simplified to show relevant patient information to a particular practitioner. Certain embodiments help provide clinical decision support to healthcare practitioners. Thus, medical errors may be reduced and surgical OR workflow may be streamlined, for example. Additionally, repetitive head and neck movements may be reduced resulting in a reduction in ergonomic difficulties.

While the invention has been described with reference to certain embodiments, it will be understood by those skilled in the art that various changes may be made and equivalents may be substituted without departing from the scope of the invention. In addition, many modifications may be made to adapt a particular situation or material to the teachings of the invention without departing from its scope. Therefore, it is intended that the invention not be limited to the particular embodiment disclosed, but that the invention will include all embodiments falling within the scope of the appended claims.

The invention claimed is:

1. A method for displaying medical information based on gaze detection, the method comprising:
   determining a direction of a user's gaze in relation to a reference position in a healthcare environment;
   identifying a user looking toward a display based on the direction of the user's gaze in relation to the reference point in the healthcare environment to establish a user identity; and
   updating medical information displayed on the display for the user based on the identity of the user, wherein the identified user is allowed to control display of information on the display.

2. The method of claim 1, where the updating step further comprises updating information on the display based on at least one of preferences and input from the user.

3. The method of claim 1, further comprising arbitrating between a plurality of users to determine control of the display in a session.

4. The method of claim 1, further comprising allowing multiple users to control information on the display in a session.

5. The method of claim 1, further comprising triggering a function at the display using at least one of a voice command, a gesture, and a gaze.

6. The method of claim 1, further comprising projecting an image into a user's oculars.

7. The method of claim 1, wherein said updating step further comprises defining at least one perspective personalizing information relevant to the user to configure the display based on the user identity.

8. The method of claim 1, further comprising filtering information available on the display based on at least one rule.

9. The method of claim 3, wherein said arbitrating step further comprises arbitrating between a plurality of users based on a set of rules to determine control of the display.

10. The method of claim 3, wherein said arbitrating step further comprises arbitrating between a plurality of users based on user priority to determine control of the display.

11. The method of claim 4, wherein said allowing step further comprises allowing multiple users to control information on the display by sharing display real estate.

* * * * *